United States Patent
Zhang

(10) Patent No.: US 7,849,753 B2
(45) Date of Patent: Dec. 14, 2010

(54) CONNECTION STRENGTH TESTING DEVICE

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 211 days.

(21) Appl. No.: 12/344,258

(22) Filed: Dec. 25, 2008

(65) Prior Publication Data

US 2010/0050781 A1 Mar. 4, 2010

(30) Foreign Application Priority Data

Sep. 3, 2008 (CN) ......................... 2008 1 0304349

(51) Int. Cl.
*G01N 3/08* (2006.01)
(52) U.S. Cl. ...................................................... 73/831
(58) Field of Classification Search .................. 73/830, 73/831, 834
See application file for complete search history.

(56) References Cited

U.S. PATENT DOCUMENTS

| 6,758,083 | B2 * | 7/2004 | Yamaguchi et al. | 73/65.03 |
| 7,673,548 | B2 * | 3/2010 | Kelly | 83/581 |
| 7,779,551 | B2 * | 8/2010 | Zhang | 33/533 |
| 7,779,552 | B1 * | 8/2010 | Zhang | 33/549 |

* cited by examiner

*Primary Examiner*—Lisa M Caputo
*Assistant Examiner*—Octavia Davis
(74) *Attorney, Agent, or Firm*—Zhigang Ma

(57) ABSTRACT

A strength testing device for testing a connection strength between a first and a second articles includes a workbench, a supporting member adjustably attached to the workbench in a vertical direction to support the first article, a blocking member adjustably attached to the workbench in a latitudinal direction to abut one side of the first article, a pair of clamping members adjustably attached to the workbench in a longitudinal direction to abut the other side of the first article, and a tester. The tester includes a blade member with a blade seating on the second article, and a suspending member holding a critical weight to break the first and second articles along a connection interface therebetween. A gravity line of the weight crosses with the blade.

12 Claims, 4 Drawing Sheets

CONNECTION STRENGTH TESTING DEVICE

BACKGROUND

1. Technical Field

The present disclosure relates to testing devices and, particularly, to a connection strength testing device.

2. Description of Related Art

In manufacturing, two articles are often connected by adhesives or soldering, for instance, rubber pads are adhesively attached to a base of a notebook computer to providing support therefor. Strength of the connection between the pads and the base may then be tested by use of a thrust meter. An operator forces the thrust meter to exert a predetermined force on the connection interface between one of the pads and the base for a certain time. However, it is not only that the testing procedure is inconvenient, but also that it is hard to get a stable and accurate connection strength value because of vibration or movement during the test.

What is needed, therefore, is to provide a connection strength testing device to overcome the above described shortcomings.

DETAILED DESCRIPTION

Figure 1:
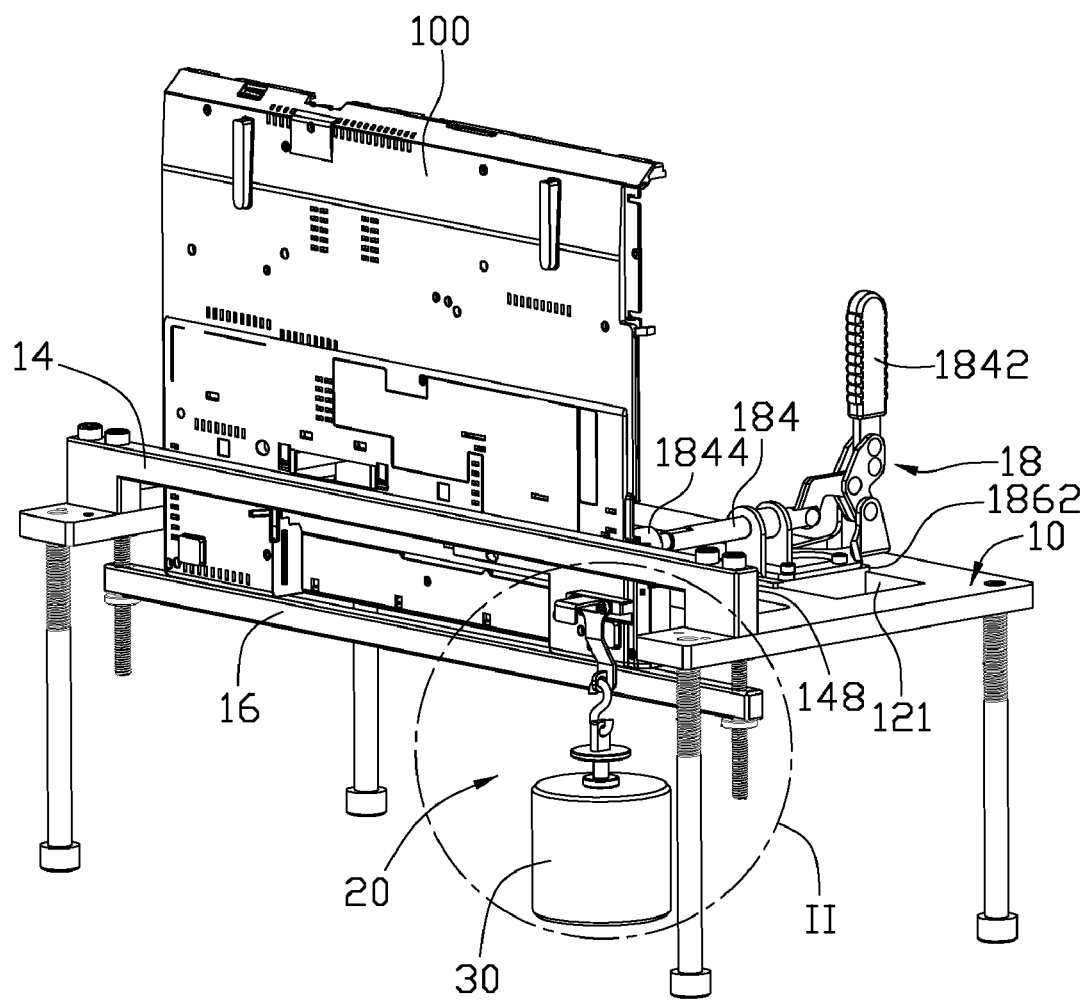
FIG. 1 is an assembled, isometric view of an embodiment of a connection strength testing device together with a first article and a second article.
Figure 2:
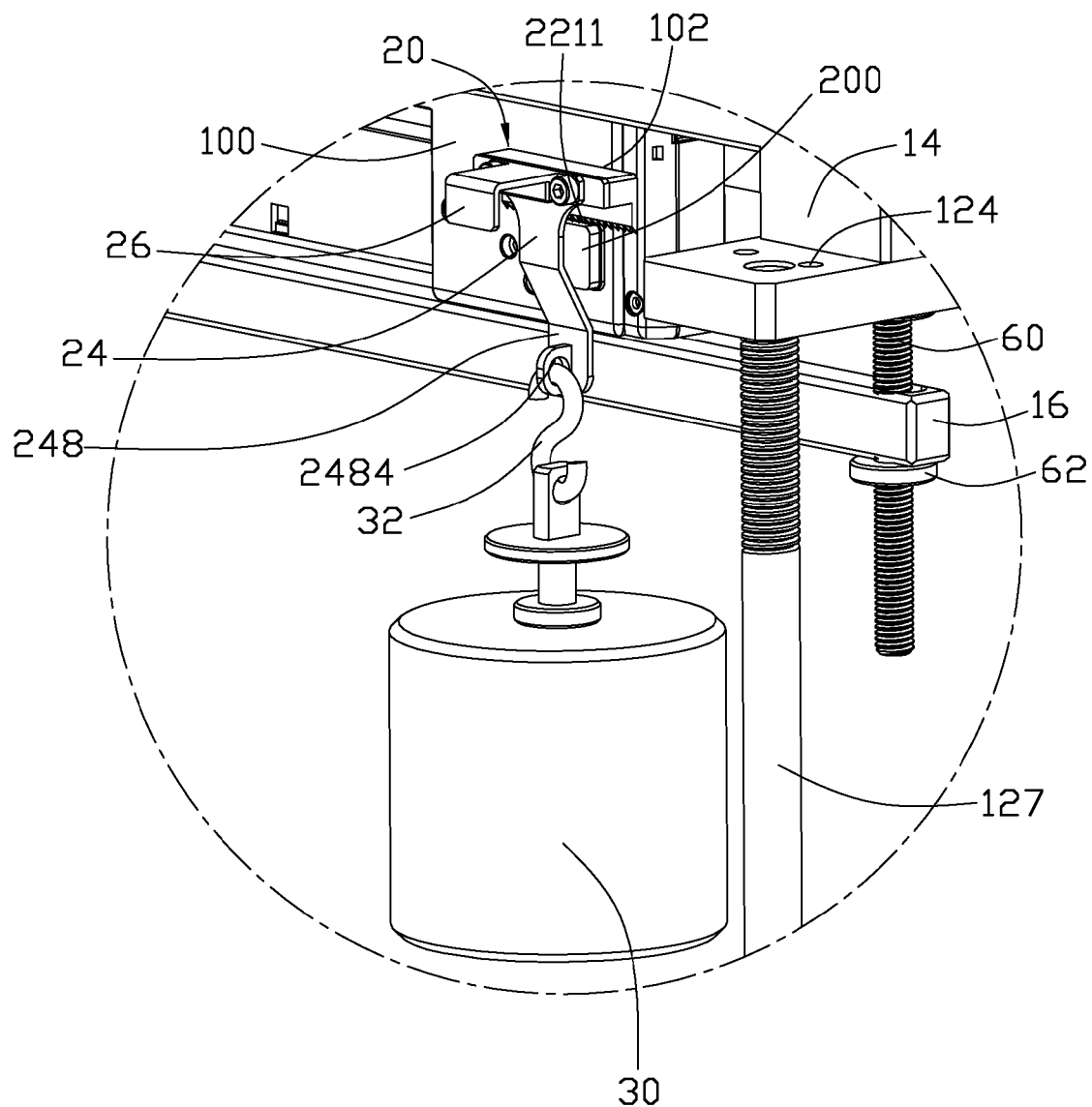
FIG. 2 is an enlarged view of the encircled portion II of FIG. 1.

Referring to FIGS. 1 and 2, an embodiment of a strength testing device for testing a connection strength between a first article 100 and a second article 200 is presented. The testing device includes a workbench 10, a supporting member 16, a blocking member 14, and a pair of clamping members 18, and a tester 20. In this embodiment, the first article 100 is a base of a notebook computer and the second article 200 is a rubber pad adhesively attached to the base.

Figure 3:
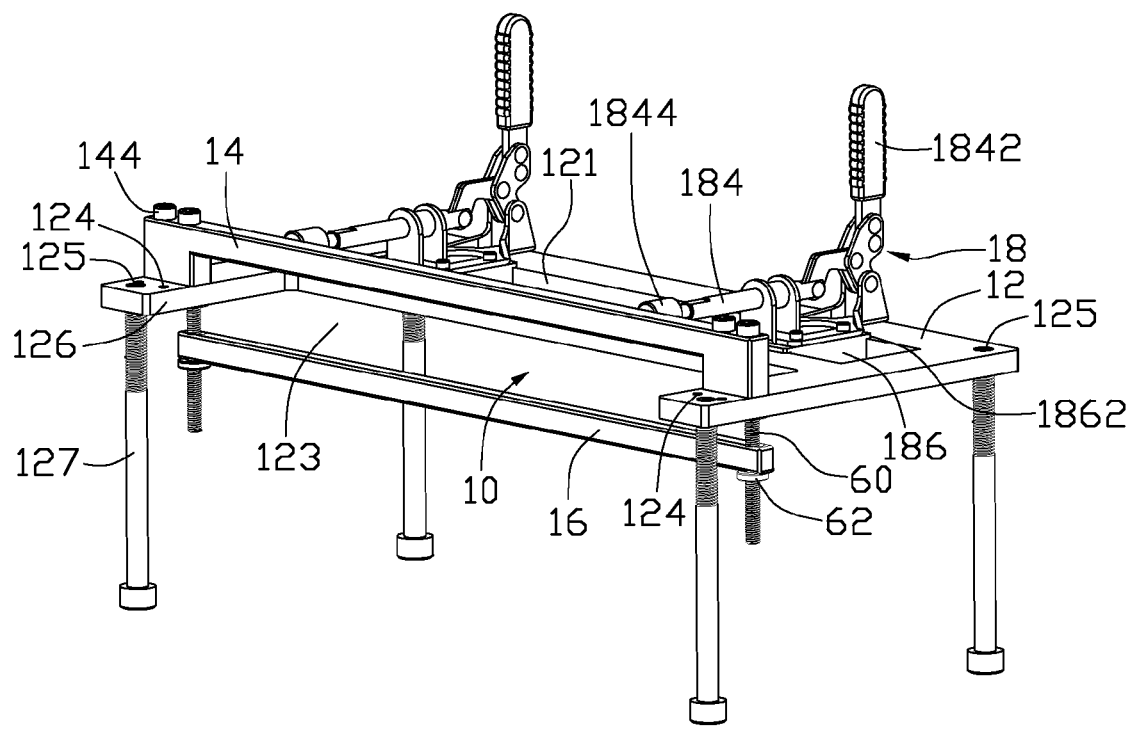
FIG. 3 is an assembled, isometric view of a workbench, a supporting member, a blocking member, and a pair of clamping members of the connection strength testing device of FIG. 1.

Referring to FIG. 3, the workbench 10 includes a plate 12, and four legs 127 adjustably attached to the plate 12. Each of the legs 127 is a bolt threadably engaging in a threaded hole 125 defined in each corner of the plate 12. A long cutout 123 is defined in the plate 12 along a front edge of the plate 12 and a pair of mounting portions 126 is formed beside two ends of the cutout 123. A long sliding slot 121 is defined in a rear portion of the plate 12, parallel to the cutout 123, for receiving the clamping members 18 therein. A plurality of pairs of threaded positioning holes 124 is symmetrically defined in each of the mounting portions 126 in a latitudinal direction (only one pair of positioning holes 124 shown in each of the mounting portions 126), allowing two pairs of bolts 144 to selectively extend therethrough to position the blocking member 14 correspondingly. A pair of fixing holes (not shown) is defined in the mounting portions 126, allowing a pair of bolts 60 to extend therethrough and engage with a pair of nuts 62 to position the supporting member 16 correspondingly.

The blocking member 14 is generally U-shaped and includes a long beam and a pair of connecting portions extending perpendicularly from opposite ends of the beam correspondingly. A pair of through holes is vertically defined in each of the connecting portions, corresponding to the positioning holes 124 of the workbench 10.

The supporting member 16 is a long bar and includes a pair of through holes defined in two ends thereof correspondingly, configured for engaging the bolts 60.

In this embodiment, the clamping members 18 are push/pull toggle clamps. The push/pull toggle clamps are well known nowadays. Each of the clamping members 18 is attached to a seat 186 and includes an operating bar 1842, an adjustable rod 184 driven by the operating bar 1842, and a resilient clamping head 1844 formed at a distal end of the rod 184. Each of the seats 186 is slidably received in the slot 121 of the workbench 10 and includes a pair of flange 1862 extending opposite therefrom to slide on the plate 12 along the slot 121.

Figure 4:
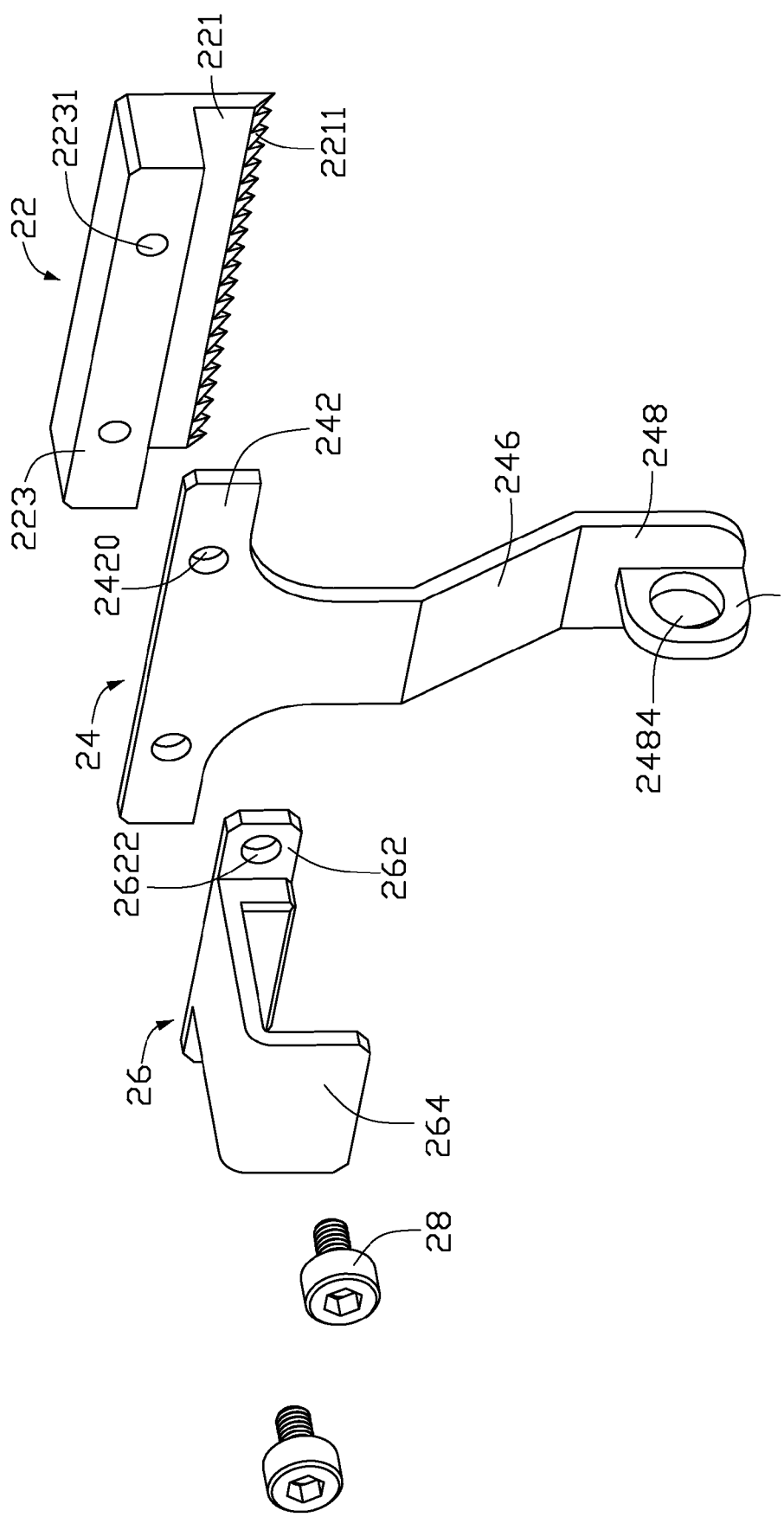
FIG. 4 is an exploded, enlarged isometric view of a tester of the connection strength testing device of FIG. 1, except a weight of the tester.

Referring to FIG. 4, the tester 20 includes a blade member 22, a suspending member 24, a handle 26, a pair of fasteners 28, and a weight 30 as shown in FIG. 1.

The blade member 22 includes a blade 221, and a protruding portion 223 extending perpendicularly from the blade 221. A plurality of teeth 2211 is formed at a distal edge of the blade 221. A pair of fixing holes 2231 is defined in the protruding portion 223.

The suspending member 24 includes a relay portion 246, a first connecting portion 242, and a second connecting portion 248. The first connecting portion 242 and the second connecting portion 248 are slantingly disposed at two opposite ends of the relay portion 246 correspondingly, extending oppositely on parallel planes. The first connecting portion 242 is generally T-shaped and includes a pair of through holes 2420 defined in a wide part thereof, corresponding to the fixing holes 2231 of the blade member 22. A holder 2482 is formed at one side of the second connecting portion 248, located between the second connecting portion 248 and an inverse extension plane of the first connecting portion 242. In this embodiment, the holder 2482 is a tab perpendicularly extending from the second connecting portion 248 and a through hole 2484 is defined in the tab for holding a critical weight 30 via a hook 32, configured for applying a force on the first article 100 or the second article 200 to break the first and second articles 100, 200 along a connection interface 102 therebetween.

The handle 26 is generally L-shaped and includes a fixing sheet 262 formed at one end thereof and a L-shaped handling portion 264. A pair of apertures 2622 is defined in the fixing sheet 262.

Referring also to FIG. 2, in assembly of the tester 20, the handle 26, the suspending member 24, and the blade member 22 are assembled, with the pair of fasteners 28 extending through the apertures 2622 of the handle 26, then the through holes 2420 of the suspending member 24 to engage in the fixing holes 2231 of the blade member 22 correspondingly. The blade member 22 is located at a first side of the suspending member 24 and the holder 2482 is located at a second side of the suspending member 24 opposite to the first side.

Referring also to FIGS. 1 and 3, in assembly of the testing device, the supporting member 16 is adjustably attached to the workbench 10 in a vertical direction, with the pair of bolts 62 sequentially extending through the fixing holes of the mounting portions 126 of the workbench 10 and the supporting member 16 to threadably engage with the nuts 62. The blocking member 14 is adjustably attached to the workbench 10 in a latitudinal direction, with the bolts 144 extending through the blocking member 14 and one pair of the positioning holes 124 of workbench 10. The clamping members 18 are adjustably attached to the workbench 10 in a longitudinal direction, with the seats 186 of the clamping members 18 slidably received in the slot 121 of the workbench 10 and located in the slot 121 by conventional threaded members, such as bolts.

In use, the plate 12 of the workbench 10 is located at a suitable height by adjusting legs 127 of the workbench 10 in the vertical direction. The first article 100 together with the second article 200 is seated on the supporting member 16 and tightly sandwiched between the blocking member 14 and the resilient heads 1844 of the clamping members 18, with the connecting interface 102 between the first article 100 and the second article 200 vertically disposed. The operating bars 1842 of the clamping members 18 are manipulated to push the resilient heads 1844 toward the blocking member 14 to abut against the first article 100 or pull the resilient heads 1844 away from the blocking member 14 to separate from the first article 100. The blade 221 of the blade member 22 is vertically seated on the second article 200. A gravity line of the weight 30 crosses at the blade 221. In this embodiment, the gravity line of the weight 30 aligns with the blade 221. Thus, the weight 30 can directly test the connection strength between the first article 100 and the second article 200.

The supporting member 14, the blocking member 16, and the clamping members 18 are adjusted in three directions to mount the first article 100 and the second article 200 on a suitable position of the workbench 10. The blade 22 of the tester 20 exerts a force on the second article 200 by the weight 30. Thus, the connection strength between the first article 100 and the second article 200 can be easily and quickly tested.

It is to be understood, however, that even though numerous characteristics and advantages of the embodiments have been set forth in the foregoing description, together with details of the structure and function of the embodiments, the disclosure is illustrative only, and changes may be made in details, especially in matters of shape, size, and arrangement of parts within the principles of the embodiments to the full extent indicated by the broad general meaning of the terms in which the appended claims are expressed.

What is claimed is:

1. A strength testing device for testing a connection strength between a first and a second articles, the testing device comprising:
   a workbench;
   a supporting member adjustably attached to the workbench and configured for supporting the first article thereon in a first direction;
   a blocking member adjustably attached to the workbench and configured for abutting a first side of the first article in a second direction perpendicular to the first direction;
   at least one clamping member adjustably attached to the workbench in a third direction perpendicular to the first and second direction, the at least one clamping member configured for abutting a second side of the first article opposite to the first side to sandwich the first article between the blocking member and the clamping member to keep a connecting interface between the first and second articles vertical; and
   a tester comprising a suspending member, and a blade member attached to the suspending member, the blade member comprising a blade configured for seating on the second article, the suspending member comprising a holder to hold a critical weight configured for applying a force on the second article to break the first and second articles along the connection interface, a gravity line of the weight crosses at the blade.

2. The strength testing device of claim 1, wherein the suspending member comprises a relay portion, a first connecting portion, and a second connecting portion, the first and the second connecting portions are slantingly disposed at two opposite ends of the relay portion, extending oppositely and paralleling to each other.

3. The strength testing device of claim 2, wherein the blade member is attached to the first connecting portion at a first side of the suspending member, the holder is attached to the second connecting portion at a second side of the suspending member opposite to the first side.

4. The strength testing device of claim 2, further comprising a handle, wherein the blade member comprises a protruding portion perpendicular to the blade, a pair of fixing holes is defined in the protruding portion, the first connecting portion is generally T-shaped, a pair of through holes is defined in a wide part of the first connecting portion, a connecting board extends from one end of the handle and defines a pair of apertures therein, a pair of fasteners sequentially extends through the apertures and the through holes to engage in the fixing holes, for assembling the handle, the suspending member, and the blade member together.

5. The strength testing device of claim 1, wherein the blade comprises a plurality of teeth formed thereon to seat the blade on the second article.

6. The strength testing device of claim 1, wherein the gravity line of the weight is substantially in alignment with a surface of the blade.

7. The strength testing device of claim 1, wherein the workbench comprises a plate and a plurality of legs adjustably attached to corners of the plate for adjusting a height of the plate.

8. The strength testing device of claim 7, wherein the plate comprises a long cutout defined therein and a pair of mounting portions formed beside two ends of the cutout.

9. The strength testing device of claim 8, wherein a pair of bolts sequentially extends through the mounting portions of the plate and two opposite ends of the supporting member to engage with a pair of nuts to locate the supporting member on the bolts.

10. The strength testing device of claim 8, wherein a plurality of pairs of threaded holes is symmetrically defined in each of the mounting portions of the plate, two pairs of bolts extends through two ends of the blocking member to selectively engage in the threaded holes for attaching the blocking member to the plate.

11. The strength testing device of claim 8, wherein the plate comprises a long slot defined therein, paralleling the cutout, the at least one clamping member is attached to a seat with a pair of flanges, the seat is slidably received in the slot, the flanges is capable of sliding on the plate.

12. The strength testing device of claim 8, wherein each of the at least one clamping member is a pull/push toggle clamp and comprises an operating bar, a rod driving by the operating bar, a resilient head is formed at a distal end of the rod to abut against the second side of the first article.

* * * * *